(12) United States Patent
Wolcott

(10) Patent No.: US 6,613,579 B2
(45) Date of Patent: Sep. 2, 2003

(54) SEQUENTIAL INJECTION LIQUID-LIQUID EXTRACTION

(75) Inventor: Duane K. Wolcott, Fox Island, WA (US)

(73) Assignee: Global FIA, Inc., Gig Harbor, WA (US)

( * ) Notice: Subject to any disclaimer, the term of this patent is extended or adjusted under 35 U.S.C. 154(b) by 247 days.

(21) Appl. No.: 09/773,464

(22) Filed: Feb. 2, 2001

(65) Prior Publication Data

US 2002/0106319 A1 Aug. 8, 2002

(51) Int. Cl.[7] .................................................. G01N 1/34
(52) U.S. Cl. ........................... 436/178; 422/81; 422/82; 422/101; 436/52; 436/53
(58) Field of Search ............................. 422/81, 82, 101; 436/52, 53, 178

(56) References Cited

U.S. PATENT DOCUMENTS

| | | | |
|---|---|---|---|
| 3,743,103 A | * 7/1973 | Isreeli et al. ............. 210/532.1 |
| 4,022,575 A | 5/1977 | Hansen et al. ............ 23/230 R |
| 4,546,088 A | * 10/1985 | Karlberg et al. ............ 436/178 |
| 4,645,647 A | 2/1987 | Yoshida et al. ............... 422/81 |
| 5,399,497 A | * 3/1995 | Kumar et al. ................. 436/53 |
| 5,516,698 A | 5/1996 | Begg et al. ................... 436/89 |
| 5,695,720 A | 12/1997 | Wade et al. .................. 422/82 |
| 5,801,302 A | 9/1998 | Riviello et al. ............ 73/61.55 |
| 5,849,592 A | 12/1998 | Pollema et al. ............... 436/52 |

* cited by examiner

*Primary Examiner*—Jan Ludlow
(74) *Attorney, Agent, or Firm*—Reginald F. Roberts, Jr.

(57) ABSTRACT

Apparatus and method for sequential injection liquid-liquid extraction analysis. Under the control of a bidirectional precision pump, a stream-selection valve, and a microprocessor, a series of liquid zones is built up in a holding/mixing coil. The liquid zones are transferred from the holding/mixing coil to a separation cell. After phase separation into an extract and a raffinate, the extract is withdrawn from the separation cell and sent to a detector, which determines the amount of a component which was extracted from a sample by an extraction solvent. The principal advantages of this automated technology are elimination of the need for dynamic phase separation; on-line pre-extraction chemical conditioning; a substantial reduction in solvent, reagent, and sample usage; and a similar substantial reduction in waste generation.

15 Claims, 4 Drawing Sheets

SEQUENTIAL INJECTION LIQUID-LIQUID EXTRACTION

BACKGROUND OF THE INVENTION

The present invention relates to instrumental chemical analysis. More particularly, the present invention relates to an automated instrumental apparatus and method for carrying out sequential injection liquid-liquid extraction. The principal advantages of this automated technology over the prior art are elimination of the need for dynamic phase separation; on-line pre-extraction chemical conditioning; a substantial reduction in solvent, reagent, and sample usage; and a similar substantial reduction in waste generation.

SUMMARY OF THE INVENTION

In general, the present invention in a first aspect provides an apparatus for sequential injection liquid-liquid extraction. The apparatus comprises (a) a bidirectional precision pump for controlling fluid flow; (b) a holding/mixing coil, for holding and mixing liquids, and carrying out liquid-liquid extraction; (c) a selection valve, for withdrawing, transferring, and injecting a plurality of fluids; (d) a separation cell, for separating an extract phase from a raffinate phase; (e) a detector, for detecting the quantity of a component which was extracted from a sample by an extraction solvent; and (f) a microprocessor, for controlling the selection valve and the bidirectional precision pump.

In a second aspect the invention provides a method for sequential injection liquid-liquid extraction. The method comprises (a) using a bidirectional precision pump under suction to transfer a sample through an inlet line to a holding/mixing coil, to purge the inlet line; (b) discharging the sample from the holding/mixing coil; (c) flushing the holding/mixing coil with a carrier solvent, to remove residual sample; (d) disposing a plurality of liquid zones in the holding/mixing coil, using a microprocessor to control the selection valve; (e) mixing the zones and providing efficient contact between an extraction solvent and the sample by passing the plurality of liquid zones through the holding/mixing coil; (f) reversing the flow through the holding/mixing coil, to provide further mixing of the zones and further liquid-liquid contact between the extraction solvent and the sample; (g) transferring the liquid zones from the holding/mixing coil to a separation cell; (h) holding the liquid zones in the separation cell, to separate an extract phase from a raffinate phase; (i) withdrawing the extract phase from the separation cell; (j) transferring the extract phase to a detector, for determining the quantity of a component extracted from the sample; and (k) determining the amount of the component extracted by measuring the response of the detector.

BRIEF DESCRIPTION OF THE DRAWINGS

FIG. 2-B is an enlarged portion of FIG. 2-A.

FIG. 3-B is a schematic representation of a portion of a separation cell containing a more-dense extract and a less-dense raffinate.

DETAILED DESCRIPTION OF THE INVENTION

Figure 1:
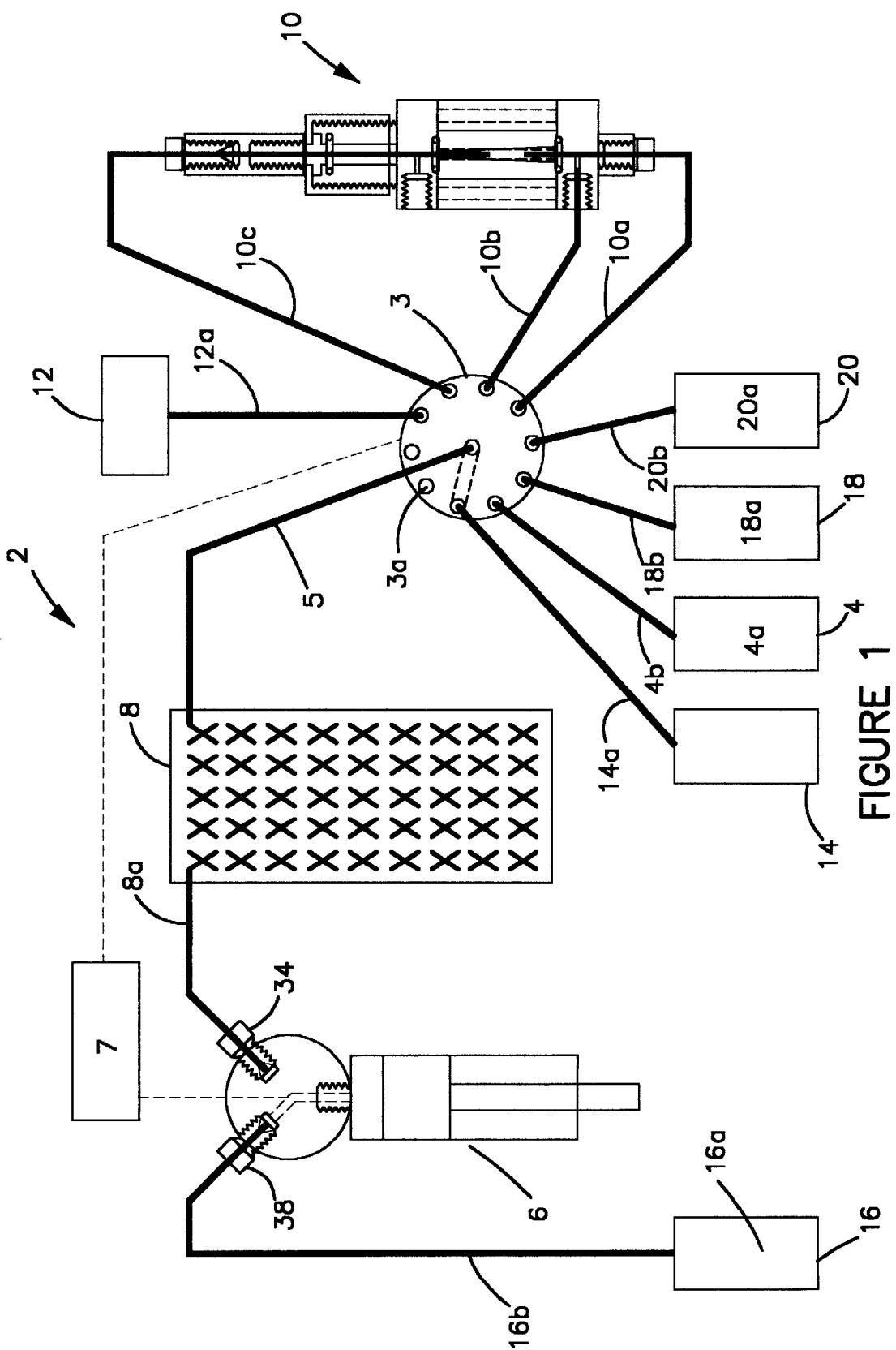
FIG. 1 is a schematic representation of an automated sequential injection, solvent extraction, and chemical analysis system, made in accordance with the principles of the present invention.

More specifically, reference is made to FIG. 1, in which is shown an analytical instrument for automated sequential injection liquid-liquid extraction, made in according with the principles of the present invention, and generally designated by the numeral 2.

The sequential injection instrument 2 comprises a syringe pump 6, a holding/mixing coil 8, a stream selection valve 3, a separation cell 10, a detector 12, and a microprocessor 7 which controls the selection valve 3 and the syringe pump 6.

By operation of the selection valve 3, a sample 4a to be analyzed is drawn from a sample container 4 through a sample line 4b under suction of the syringe pump 6. The sample 4a is drawn through an inlet line 5 into the holding/mixing coil 8, to purge the inlet line 5 with fresh sample 4a. The flow of sample 4a into the holding/mixing coil 8 is stopped when the inlet line 5 has been adequately flushed to remove any trace of a previous sample.

The selection valve 3 is switched to a waste line 14a leading to a waste reservoir 14. Excess sample 4a in the holding/mixing coil 8 is pushed out to the waste reservoir 14, followed by an excess of carrier solvent 16a, previously drawn into the syringe pump 6 from a solvent container 16 through a solvent line 16b. The selection valve 3 is switched to the solvent line 16b connected to the solvent container 16 filled with a carrier solvent 16a. A sufficient quantity of the carrier solvent 16a is used to flush any residual sample 4a out of the holding/mixing coil 8. The carrier solvent 16a always fills the syringe pump 6.

Preparation of the separation cell 10 is effected by washing all lines 10a, 10b, 10c connected thereto with the carrier solvent 16a from the solvent container 16. The cell 10 is then drained by drawing off the waste carrier solvent 16a through lines 10b and 5 into the holding/mixing coil 8 under suction of the syringe pump 6. The selection valve 3 is then switched to line 14a, and the waste carrier solvent 16a is pushed out to the waste reservoir 14 under pressure from the syringe pump 6, followed by sufficient excess carrier solvent 16a to adequately flush the holding/mixing coil 8. After washing the separation cell 10, lines 10a, 10b, and 10c may be filled with carrier solvent 16a or air as required by a particular methodology.

Figure 2A:
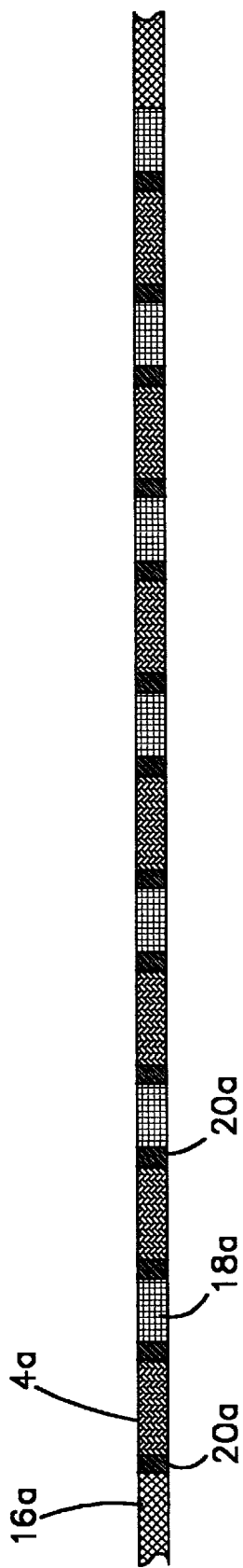
FIG. 2-A is a schematic representation of a series of liquid zones in a holding/mixing coil.
Figure 2B:
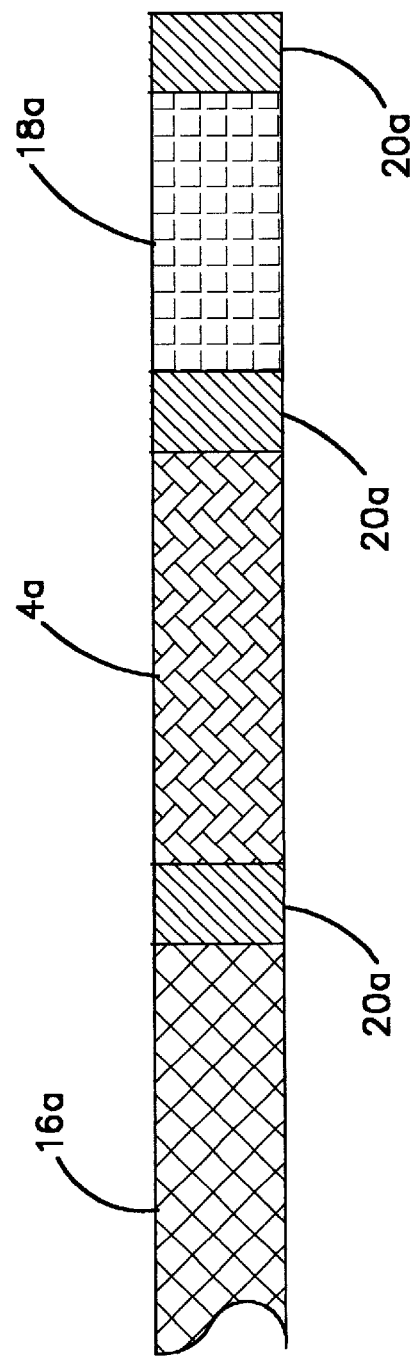

After the separation cell 10 has been prepared, the selection valve 3 and syringe pump 6 are manipulated, under the control of the microprocessor 7, to stack a series of liquid zones in the holding/mixing coil 8. FIGS. 2-A and 2-B show a typical profile of the holding/mixing coil 8 stacked with a plurality of liquid zones. A conditioning chemical 20a, drawn from a chemical container 20 through a chemical conditioner line 20b, is included in the stack of liquid zones, along with the carrier solvent 16a, sample 4a, and extraction solvent 18a drawn through line 18b.

Referring again to FIG. 1, the selection valve 3 is switched to a port 3a open to the atmosphere, and the zone stack is withdrawn under pump 6 suction into the holding/mixing coil 8. This movement results in mixing the zones, and in efficient contact of the sample 4a with the extraction solvent 18a.

When the leading edge of the first zone reaches the end 8*a* of the holding/mixing coil 8, flow is stopped, then reversed, pushing the zone stack shown in FIGS. 2-A and 2-B back through the holding/mixing coil 8. This operation results in further zonal mixing. It will be apparent to those skilled in the art that the forward-reverse mixing action can be repeated as many times as required to achieve any desired degree of agitation and any desired time of interphase contact. If only one mixing cycle is required, or at the end of the required number of mixing cycles, the zone stack is pushed out of the holding/mixing coil 8 through a port of the selection valve 3 connected to the inlet line 10*a* of the separation cell 10.

After the zones have been transferred from the holding/mixing coil 8 to the separation cell 10, the selection valve 3 is switched to a port connected to line 14*a* leading to the waste reservoir 14. Additional carrier solvent 16*a* is conveyed to the waste reservoir 14 through the holding/mixing coil 8 to remove any remaining trace of either the sample 4*a* or the extraction solvent 18*a* which might have adhered to the walls of the holding/mixing coil 8.

Figure 3A:
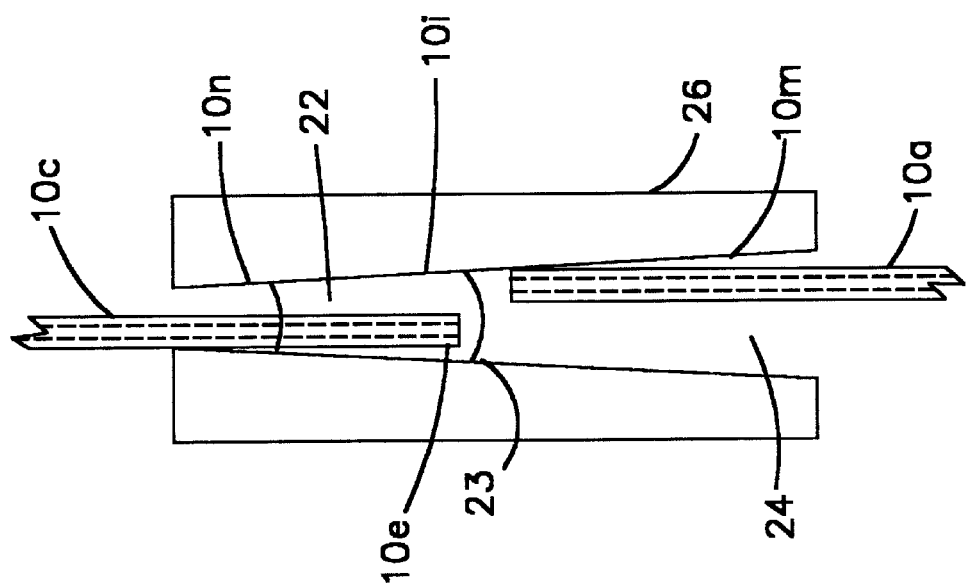
FIG. 3-A is a schematic representation of a portion of a separation cell containing a less-dense extract and a more-dense raffinate, made in accordance with the principles of the present invention.
Figure 3B:
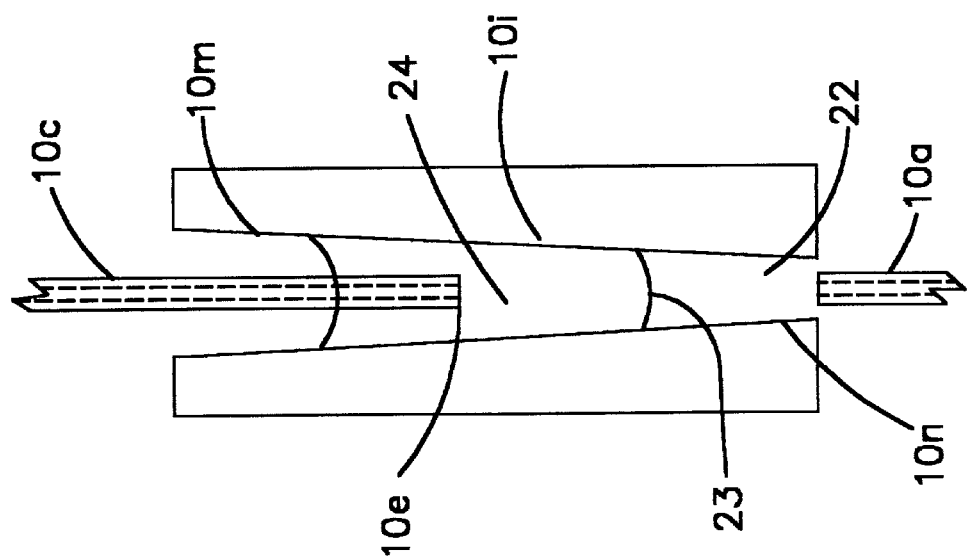

The immiscible zones are allowed to stand in the separation cell 10 as long as necessary to complete phase separation into an extract 22 and a raffinate 24, as depicted in FIGS. 3-A and 3-B. During this "static" separation period of time, other parts of the sequential injection instrument 2 can be processed; e.g., the holding/mixing coil 8 can be solvent-washed.

Figure 4:
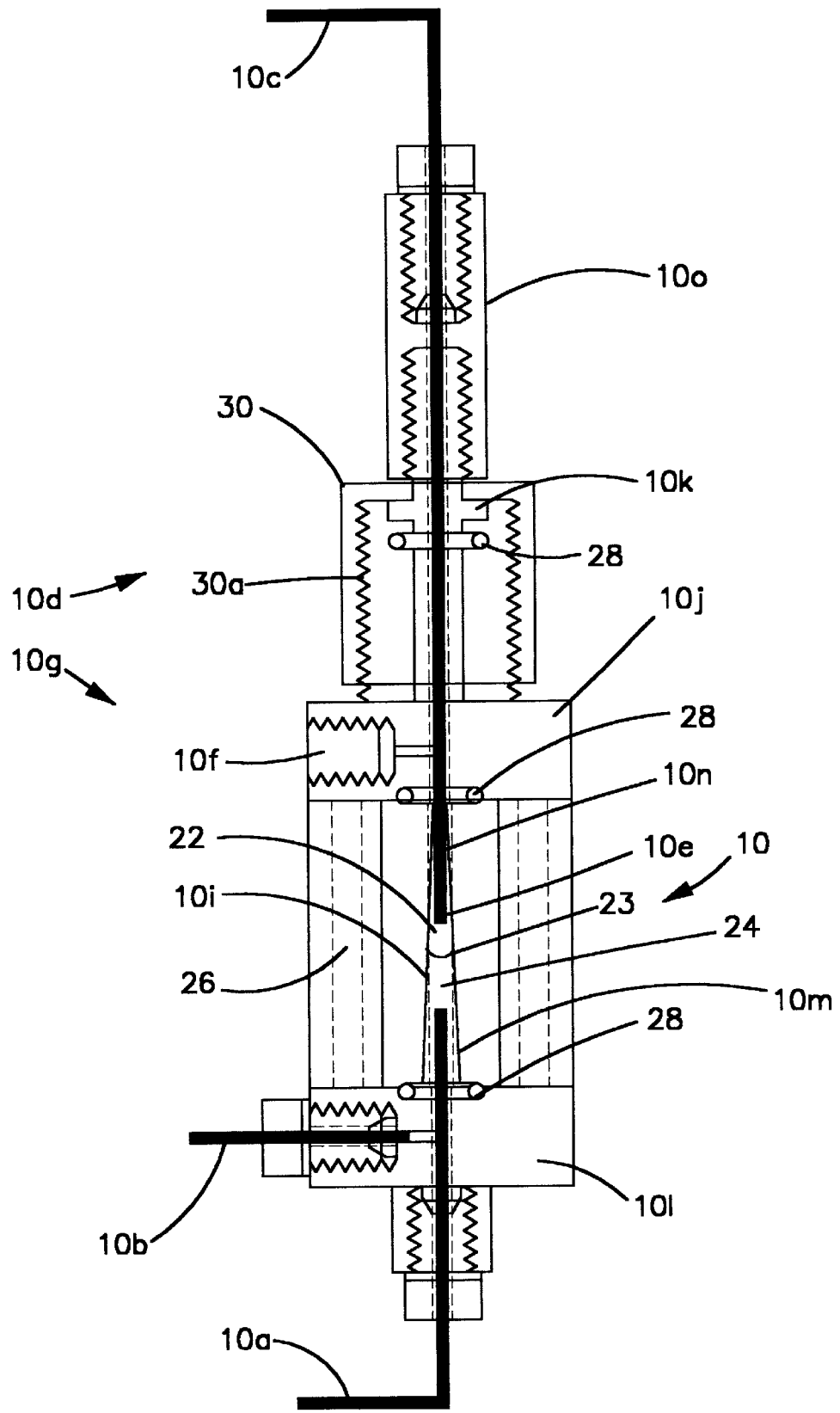
FIG. 4 is a schematic representation of a separation cell, made in accordance with the principles of the present invention.

Reference is now made to FIG. 4, in which are shown further details of the separation cell 10.

After phase separation is complete, and if the extract 22 is less dense than the raffinate 24, as illustrated in FIG. 3-A, the selection valve 3 is switched to a port connecting the holding/mixing coil 8 to an upper portion 10*d* of the separation cell 10 through line 10*c*, the tip 10*e* of which is disposed just above the meniscus 23 defined by the two phases 22 and 24. The extract 22 is withdrawn into the line 10*c*. The tip 10*e* of line 10*c* is then exposed to air drawn from a lateral port 10*f* in the upper portion 10*d* of the separation cell 10. As suction continues, pulling the extract 22 into the holding/mixing coil 8, air fills the line 10*c* behind the extract 22, thereby minimizing or preventing dilution by solvent or other liquids. After all of the extract 22 withdrawn has been transferred to the holding/mixing coil 8, and before any air enters the selection valve 3 port, flow is stopped.

Referring again to FIG. 1, the selection valve 3 is switched to a port connecting the holding/mixing coil 8 to the detector 12 through line 12*a*, and the extract 22 is conveyed to and through a flowcell (not shown) of the detector 12, followed by a sufficient volume of the carrier solvent 18*a* to ensure that the flowcell has been contacted by all of the extract 22 which has been withdrawn, thereby generating a detectable and quantitative peak response.

The selection valve 3 (FIG. 1) is switched to the line 10*b* connecting the holding/mixing coil 8 to a lower portion 10*g* of the separation cell 10 (FIG. 4), and the raffinate 24 is withdrawn into the holding/mixing coil 8 through the inlet line 5 under syringe pump 6 suction.

Referring to FIG. 1, the selection valve 3 is switched to a port connecting the holding/mixing coil 8 to the waste reservoir 14 via lines 5 and 14*a*, and the raffinate 24 and any remaining extract 22 are jettisoned to the waste reservoir 14. The holding/mixing coil 8 is then flushed out with the carrier solvent 16*a*.

The selection valve 3 is then manipulated to flush all lines 10*a*, 10*b*, and 10*c* connected to the separation cell 10 with the carrier solvent 16*a*, and to fill the separation cell 10 with the carrier solvent 16*a*. The carrier solvent 16*a* is then withdrawn from the separation cell 10 via line 10*b* into the holding/mixing coil 8, and then sent to the waste reservoir 14 via line 14*a*. This procedure effectively washes the separation cell 10, thereby preventing sample-to-sample carryover.

If the extract 22 is more dense than the raffinate 24, as illustrated in FIG. 3-B, the above procedure is modified as follows. Following phase separation, the selection valve 3 is switched to a port connecting the holding/mixing coil 8 to the lower portion 10*g* of the separation cell 10 through line 10*b*. The extract 22 is withdrawn into the line 10*b* and transferred to the holding/mixing coil 8 through line 5.

The selection valve 3 is switched to a port connecting the holding/mixing coil 8 to the detector 12 through line 12*a*, and the extract 22 is conveyed to and through the flowcell (not shown) in the detector 12, followed by a sufficient quantity of the carrier solvent 18*a* to ensure that the flowcell has been contacted with all of the extract 22 which has been withdrawn, generating a detectable and quantitative peak response.

The selection valve 3 is switched to a port connecting the holding/mixing coil 8 to the lower portion 10*g* of the separation cell 10 through line 10*b*. The raffinate 24 is withdrawn into line 10*b* and transferred to the holding/mixing coil 8 through line 5, thence to the waste reservoir 14 by switching the selection valve 3 to a port connecting the holding/mixing coil 8 to line 14*a*.

The remaining procedure is similar to that described for the case in which the extract 22 is less dense than the raffinate 24.

Reference is now made to FIG. 4, in which is shown a detailed representation of the separation cell 10.

The separation cell 10 includes a tapered container 10*i* mounted in and to a first housing 26 by O-rings 28, a first end cap 10*j*, an adjustment fitting 10*k*, and a second end cap 101.

The adjustment fitting 10*k* is a very important part of the present invention. By means of the adjustment fitting 10*k*, which is slidably fitted into the end cap 10*j*, the line 10*c* can be raised or lowered to position the tip 10*e* just above the meniscus 23. An adjustment nut 30 riding on threads 30*a* rides in a groove formed by a raised ring on the fitting 10*k* and tube union 10*o*. Only line 10*c* is so adjustable. Line 10*a* is fixed in place.

FIGS. 3-A and 3-B actually depict two different dispositions of the tapered container 10*i*, depending on whether the raffinate 24 is heavier or lighter than the extract 22, which is typically of smaller volume.

Referring now to FIGS. 3-A, 3-B, and 4, the tapered container 10*i* has first and second ends 10*m* and 10*n*. The container 10*i* is constructed and arranged to hold the extract 22 and raffinate 24. The container 10*i* is preferably made of glass, and tapers from wide to narrow in a direction away from the first end 10*m* toward the second end 10*n*. The tapered container 10*i* is so arranged that the narrower second end 10*n* is pointed in a direction facilitating removal of the phase having the smaller volume—typically the extract. If the extract 22 is less dense than the raffinate 24 (FIG. 3-A), the container 10*i* is disposed vertically with the first end 10*m* of the container 10*i* below the second end 10*n* of the container 10*i*. If the extract 22 is more dense than the raffinate 24 (FIG. 3-B), the container 10*i* is disposed vertically with the first end 10*m* of the container 10*i* above the second end 10*n* of the container 10*i*. In either case, the container 10*i* is oriented so that the extract 22 is disposed in the second end 10*n* of the container 10*i*, and the raffinate 24 is disposed in the first end 10*m* of the container 10*i*. It will be apparent to those skilled in the art that this arrangement optimizes and maximizes efficient withdrawal of the extract 22.

The syringe pump 6 is connected to the holding/mixing coil 8 by a line 8*a* disposed in a first fitting 34, to the solvent container 16 by line 16*b* disposed in a second fitting 38, and to the selection valve 3 by the microprocessor 7.

While certain embodiments and details have been described to illustrate the present invention, it will be apparent to those skilled in the art that many modifications are possible without departing from the scope and basic concept of the invention. For example, a selection valve with more ports would allow use of a plurality of extraction solvents, addition of different wash liquids, and addition of various standard solutions.

I claim:

1. An apparatus for sequential injection liquid-liquid extraction, the apparatus comprising:
   (a) a bidirectional precision pump for controlling fluid flow;
   (b) a holding/mixing coil, connected to the pump, for holding and mixing liquids, and for carrying out liquid-liquid extraction;
   (c) a selection valve, connected to the pump, for directing flow to withdraw, transfer, and inject a plurality of fluids;
   (d) a separation cell, for separating liquids from the holding/mixing coil into an extract phase and a raffinate phase;
   (e) a detector, for determining the quantity of a component in the extract phase which was extracted from a sample by an extraction solvent; and
   (f) a microprocessor, for controlling the selection valve and the bidirectional pump;
the separation cell including a container for holding the extract and raffinate phases, a first passageway for conveying the extract and raffinate from the holding/mixing coil to the container, a second passageway for conveying the extract phase from the container to the detector and an adjustment fitting which enables raising and lowering the second passageway precisely as required for efficient withdrawal of the extract phase.

2. An apparatus for sequential injection liquid-liquid extraction, the apparatus comprising:
   (a) a bidirectional pump for controlling fluid flow;
   (b) a holding/mixing coil, connected to the pump, for holding and mixing liquids, and carrying out liquid-liquid extraction;
   (c) a selection valve, connected to the pump, for directing flow to withdraw, transfer, and inject a plurality of fluids;
   (d) a separation cell, constructed and arranged for vertical orientation and for static retention of liquids therein, for separating liquids from the holding/mixing coil into an extract phase and a raffinate phase;
   (e) a detector, for determining the quantity of a component in the extract phase which was extracted from a sample by an extraction solvent; and
   (f) a microprocessor, for controlling the selection valve and the bidirectional pump;
the separation cell including a container for holding the extract and raffinate stationary until phase separation is complete, a first passageway for conveying the extract and the raffinate from the holding/mixing coil to the container, and a second passageway for conveying the extract phase from the container to the detector,
   wherein the microprocessor is operative to stop flow through the separation cell during separation of liquids from the holding/mixing coil into an extract phase and a raffinate phase.

3. The apparatus of claim 2, wherein the apparatus is constructed and arranged to recover the extract phase by positioning the selection valve to cause the pump to withdraw the extract phase through the second passageway.

4. The apparatus of claim 2, wherein the container has first and second ends, and tapers from wide to narrow in a direction away from the first end toward the second end.

5. The apparatus of claim 4, wherein the separation cell is constructed and arranged so that the first passageway enters the first end of the container, the second passageway enters the second end of the container, the raffinate phase is disposed in the first end of the container, and the extract phase is disposed in the second end of the container.

6. The apparatus of claim 5, wherein the separation cell is constructed and arranged so that, when the extract phase is less dense than the raffinate phase, the container is disposed vertically with the first end of the container below the second end of the container.

7. The apparatus of claim 5, wherein the separation cell is constructed and arranged so that, when the extract phase is more dense than the raffinate phase, the container is disposed vertically with the first end of the container above the second end of the container.

8. A method for sequential injection liquid-liquid extraction, the method comprising the steps of:
   (a) using a bidirectional precision pump under suction to transfer a sample through an inlet line to a holding/mixing coil, to purge the inlet line;
   (b) discharging the sample from the holding/mixing coil;
   (c) flushing the holding/mixing coil with a carrier solvent, to remove residual sample;
   (d) disposing a plurality of liquid zones in the holding/mixing coil, using a microprocessor to control a selection valve;
   (e) mixing the zones and providing efficient contact between an extraction solvent and the sample, by passing the plurality of liquid zones through the holding/mixing coil;
   (f) reversing the flow through the holding/mixing coil, to provide further mixing of the zones and further liquid-liquid contact between the extraction solvent and the sample;
   (g) transferring the liquid zones from the holding/mixing coil to a separation cell;
   (h) holding the liquid zones in the separation cell, to separate an extract phase from a raffinate phase;
   (i) withdrawing the extract phase from the separation cell;
   (j) transferring the extract phase to a detector, for determining the quantity of a component extracted from the sample; and
   (k) determining the amount of the component extracted by measuring the response of the detector.

9. The method of claim 8, wherein the separation cell includes a container for holding the extract and raffinate phases, a first passageway for conveying the extract and raffinate phases to the container, and a second passageway for conveying the extract phase from the container.

10. The method of claim 9, wherein the separation cell includes an adjustment fitting which enables raising and lowering of the second passageway for efficient withdrawal of the extract phase.

11. The method of claim 8, wherein the separation cell includes a tapered container for holding the extract and raffinate phases, a first passageway for conveying the extract and raffinate phases to the container, and a second passageway for conveying the extract phase from the container.

12. The method of claim 11, wherein the container has first and second ends, and tapers from wide to narrow in a direction away from the first end toward the second end.

13. The method of claim 12, wherein the separation cell is constructed and arranged so that the first passageway enters the first end of the container, the second passageway enters the second end of the container, the raffinate phase is disposed in the first end of the container, and the extract phase is disposed in the second end of the container.

14. The method of claim 13, wherein the separation cell is constructed and arranged so that, when the extract phase is less dense than the raffinate phase, the container is disposed vertically with the first end of the container below the second end of the container.

15. The method of claim 13, wherein the separation cell is constructed and arranged so that, when the extract phase is more dense than the raffinate phase, the container is disposed vertically with the first end of the container above the second end of the container.

* * * * *